United States Patent

Wahnish

[11] 4,060,896
[45] Dec. 6, 1977

[54] PROSTHODONTIC IMPLANT AND METHOD

[76] Inventor: M. Ervin Wahnish, 612 E. Church St., Orlando, Fla. 32801

[21] Appl. No.: 689,102

[22] Filed: May 24, 1976

[51] Int. Cl.² .................................................. A61L 13/00
[52] U.S. Cl. ................................................................ 32/10 A
[58] Field of Search ................................ 3/1.9; 32/10 A

[56] References Cited

U.S. PATENT DOCUMENTS

| | | | |
|---|---|---|---|
| 2,112,007 | 3/1938 | Adams | 32/10 A |
| 2,347,567 | 4/1944 | Kresse | 32/10 A |
| 3,672,058 | 6/1972 | Nikoghossian | 32/10 A |
| 3,717,932 | 2/1973 | Brainin | 32/10 A |

Primary Examiner—Robert Peshock
Attorney, Agent, or Firm—Duckworth, Hobby & Allen

[57] ABSTRACT

A prosthodontic implant for anchoring dental appliances to a jawbone implant site, includes a filler of a non-rejectable, hardenable material disposed in the jawbone socket, with a threaded screw of a non-rejectable material extending axially into the site and through the filler, the screw dimensioned such that the outer diameter thereof engages a portion of the periphery of the jawbone socket. The filler is interposed between portions of the screw and the periphery of the socket.

9 Claims, 2 Drawing Figures

PROSTHODONTIC IMPLANT AND METHOD

BACKGROUND OF THE INVENTION

1. Field of the Invention

The present invention relates to dental appliances, and in particular relates to prosthodontic implants for anchoring dental appliances in either a natural or prepared jawbone socket.

2. Description of the Prior Art

A plurality of implant anchors for dental appliances have been developed in the prior art. For example, in U.S. Pat. No. 2,112,007, Adams discloses an anchoring appliance for false teeth employing a threaded rod extending into a thimble made of a nonelectrolytic metal, such as silver.

In U.S. Pat. No. 2,347,567, Kresse discloses a dental implant formed of a plastic material, such as methyl methacrylate, for example. The implant disclosed by Kresse has a frustro-conical shape, and is threaded on the outer surface thereof to engage the sides of a jawbone socket.

Rauscher, in U.S. Pat. No. 2,835,035, also discloses a polyethyl methacrylate implant having a threaded outer surface, and a mechanism for installing the implant.

In U.S. Pat. No. 3,590,485, Chercheve et al. disclose a dental implant having a central metallic rod encircled by a sleeve cut from a solid animal tooth, the outer periphery of the animal tooth having undulations therein for engaging the periphery of a jawbone socket.

Another arrangement is disclosed by Gillespie in U.S. Pat. No. 1,408,582, and also includes a threaded screw adapted to extend into the jawbone. Other such arrangements are disclosed in U.S. Pat. No. 2,609,604 to Sprague; and U.S. Pat. No. 3,797,113 to Brainin.

SUMMARY OF THE INVENTION

The present invention comtemplates a prosthodontic implant for anchoring dental appliances in a jawbone socket, and comprises a filler of a non-rejectable, hardenable material disposed in the jawbone socket, with a shaft of a non-rejectable material extending axially into the socket and through the filler, said shaft having undulations along the outer periphery thereof and dimensioned such that the outer periphery engages a portion of the periphery of the jawbone socket. The filler is interposed between portions of the shaft and the periphery of the jawbone socket. In use, the filler is allowed to harden and fill any voids between the outer periphery of the shaft and the periphery of the jawbone socket, thereby affording immediate stabilization of the shaft.

In the preferred embodiment, the filler consists essentially of a material selected from the group consisting of poly-methyl methacrylate and methyl methacrylate.

THE DRAWING

DETAILED DESCRIPTION

The implant of the present invention, and the method for using same, will be described with reference to FIGS. 1 and 2.

Figure 1:
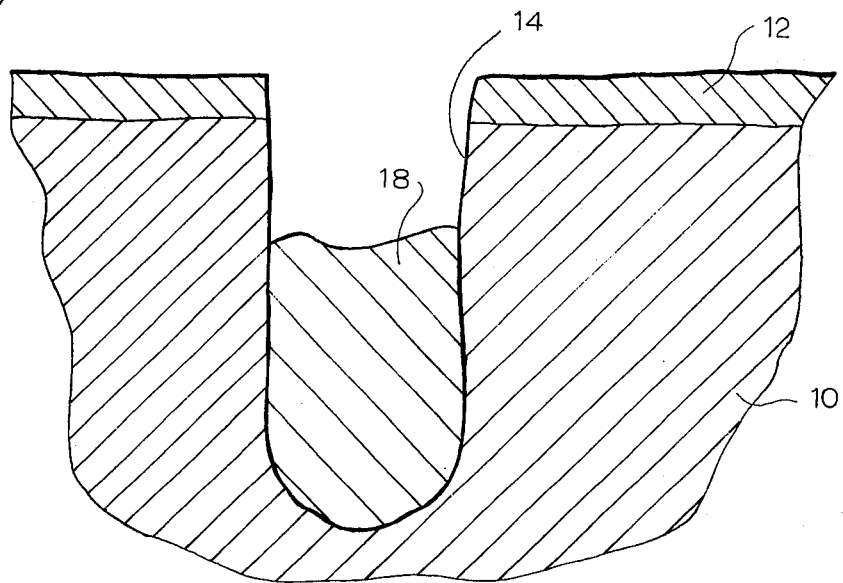
FIG. 1 is a cross-section of a jawbone socket which has been prepared to receive a prosthodontic implant in accordance with the present invention.
Figure 2:
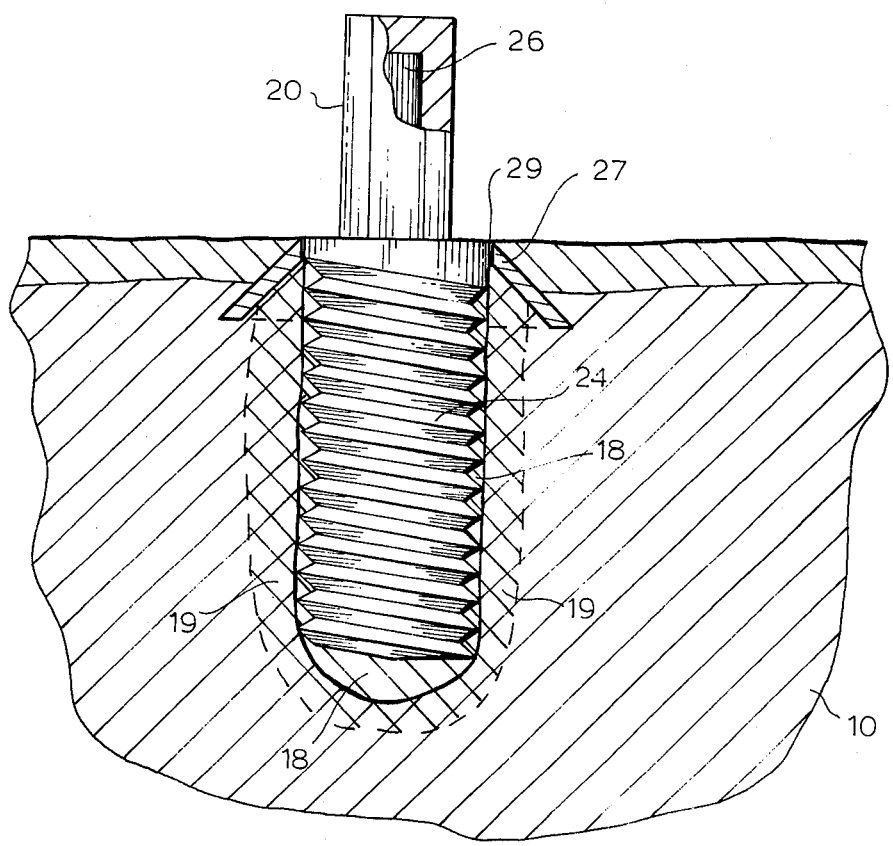
FIG. 2 is a cross-section like that of FIG. 1, with the implant device in place, and with a portion of the implant shown cut away.

Referring first to FIG. 1, a portion of the human jawborn 10 is shown in cross-section, with the gingival mucosa 12 overlying the surface of the jawbone. A jawbone implant site 14 extends through the mucosa 12 and into the jawbone 10. This site, or socket 14 is usually prepared by a drill or similar tool having a specific outer diameter which is essentially the same as the desired diameter of the jawbone socket 14 as it passes through the gingival mucosa 12.

In accordance with the present invention, a filler 18 of an amorphous, hardenable and non-rejectable material is inserted within the jawbone socket 14. Thereafter, an implant device, such as a threaded screw 20, is installed in the jawbone socket 14. In this example, this is accomplished by threading the screw 20 into the jawbone socket 14 through the gingival mucosa 12 and into the jawbone 10. It will, of course, be understood by those skilled in the art that the outer diameter of the threaded portion 24 of the screw 20 is selected to correspond to the size of the jawbone socket 14 as it passes through the gingival mucosa 12. The threaded periphery 24 of the screw 20 therefore engages a major portion of the sides of the jawbone socket 14. The pressure of the threaded periphery 24 of the screw 20 into the jawbone socket 14 causes the filler material 18 to compress against the periphery of socket 14. In turn, the filler 18 is compressed into the immediately adjacent area of the jawbone 10, as noted by the double cross-hatched area 19 in FIG. 2. The filler material 18 is then allowed to harden, thereby firmly holding the screw 20 in the jawbone socket 14, as the screw 20 and the filler material 18 become homogenous. It will be appreciated that any excess of the filler material 18 which pours out of the jawbone socket 14 after insertion of the screw 20 is immediately wiped away, in order to prevent the hardening of that excess material after insertion of the screw 20.

It will thus be appreciated that the filler 18 forms a firm bond between the jawbone 10 and the screw 20.

In accordance with another aspect of this invention, the filler material 18 and the implant screw 20 are both of a material which is selected from the group consisting of poly-methyl methacrylate and methyl methacrylate. Further, as is shown in the cut-away portion of the head of the screw 20 in FIG. 2, the screw includes a support rod 26 imbedded within the screw, the rod preferably comprising titanium or vitalium or any tissue acceptable metal, having a roughened outer surface in order to allow the screw 20 to be cast in firm contact with the rod 26.

Although not essential, further structural support may be provided to the device by use of a circumferential stabilizer 27 which comprises a beveled washer having a conical shape. The stabilizer 27 has an aperture 29 therethrough for accepting the screw 20, and is dimensioned so as to be capable of extending below the mucosa 12 upon exertion of appropriate pressure. It will be understood that the stabilizer 27 may be removed, if desired, after the filler 18 has hardened.

The arrangement shown in the drawings and described above provides a facile method for implanting a prosthodontic device, and in which the filler material 18 provides a firm anchor to the jawbone socket 14 after that material is allowed to harden. It will, of course, be understood that the dentist would avoid any stress against the upper portion of the screw 20 until such time as the filler material 18 has been allowed to harden and form a strong, homogenous bond between the periphery of the jawbone socket 14 and the threaded periphery 24 of the screw 20.

I claim:

1. A prosthodontic implant for anchoring dental appliances in a jawbone socket, comprising:
    a filler of a non-rejectable, hardenable material selected from the group consisting of poly-methyl methacrylate and methyl methacrylate disposed in said jawbone socket;
    a member of a non-rejectable material selected from the group consisting of poly-methyl methacrylate and methyl methacrylate extending into said socket and through said filler, said member having undulations along the outer periphery thereof and dimensioned such that a portion of the outer periphery thereof engages a portion of the periphery of said jawbone socket; and wherein
    said filler is interposed between portions of said shaft and the periphery of said jawbone socket and is homogenous with said shaft.

2. The implant recited in claim 1 wherein said filler comprises a non-rejectable, hardenable material selected from the group consisting of poly-methyl methacrylate and methyl methacrylate.

3. The implant recited in claim 1 wherein said shaft comprises a non-rejectable, hardened material selected from the group consisting of poly-methyl methacrylate and methyl methacrylate.

4. The implant recited in claim 1 wherein said shaft comprises a threaded screw.

5. The implant recited in claim 4 further comprising a structural supporting rod extending through the portion of said screw, said rod extending substantially axially with said screw.

6. The implant recited in claim 5 wherein said screw consists essentially of a methacrylate compound completely surrounding said supporting rod.

7. The implant recited in claim 6 wherein said rod comprises a metal.

8. The implant recited in claim 7 wherein said screw further includes a hexagonal head extending above said jawbone socket and covering said mucosa.

9. The implant recited in claim 8 further including a circumferential stabilizer surrounding said screw and contacting said jawbone.

* * * * *